(12) United States Patent
Kern et al.

(10) Patent No.: US 6,927,281 B1
(45) Date of Patent: Aug. 9, 2005

(54) ADENO-ASSOCIATED VIRUS-ITS DIAGNOSTIC USE WITH EARLY ABORTION

(75) Inventors: Andrea Kern, Inlingen (DE); Jürgen Kleinschmidt, Bammental (DE); Karsten Geletneky, Heidelberg (DE); Michéle Rabreau, Bordeaux (FR); Jörg Schlehofer, Leimen (DE); Edda Tobiasch, Dossenheim (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 08/637,752

(22) PCT Filed: Oct. 28, 1994

(86) PCT No.: PCT/EP94/03564

§ 371 (c)(1), (2), (4) Date: Jul. 20, 2001

(87) PCT Pub. No.: WO95/11997

PCT Pub. Date: May 4, 1995

(30) Foreign Application Priority Data

Oct. 28, 1993 (EP) .................................. 93117452

(51) Int. Cl.$^7$ ............................................. C07K 16/08
(52) U.S. Cl. ................................. 530/388.3; 530/389.4; 435/5
(58) Field of Search .......................... 530/388.3, 389.4; 435/5

(56) References Cited

U.S. PATENT DOCUMENTS 6,093,534 A * 7/2000 Shimada et al. ................ 435/5
6,489,162 B1 * 12/2002 Shenk et al. ................. 435/325

FOREIGN PATENT DOCUMENTS

| WO | WO 91/04330 | 4/1991 |
|----|-------------|--------|
| WO | WO 91/12269 | 8/1991 |

OTHER PUBLICATIONS

Hunter et al. Journal of Virology 66(1): 317–324, 1992.*
Hoggan et al. Proceedings of the National Academy of Sciences USA 55:1467–1474, 1966.*
Georg–Fries et al. Virology 134:64–71, 1984.*
Lipps et al. Infection and Immunity 37(1): 200–204, 1982.*
Dreizin et al. Voprsy Virologii 1977, (1) p. 8207, abstract only cited.*
Berns et al., 1987, "Adeno–Associated Viruses: An Update," *Adv. Virus Res. 32*:243–306.

de La Maza et al., 1980, "Heavy and Light Particles of Adeno–Associated Virus," *J. Virol. 33*:1129–1137.
Dürst et al., 1992, "Human Papillomavirus Type 16 (HPV 16) Gene Expression and DNA Replication in Cervical Neoplasia: Analysis by in Situ Hybridization," *Virology 189*:132–140.
Klein–Bauernschmitt et al., 1992, "Induction of Differentiation–Associated Changes in Established Human Cells by Infection with Adeno–Associated Virus Type 2," *J. Virol. 66*:4191–4200.
Laird et al., 1991, "Simplified Mammalian DNA Isolation Procedure," *Nucleic Acids Res. 19*:4293–4294.
Rogers et al., 1993, "Detection of Human Parvovirus B19 in Early Spontaneous Abortuses Using Serology Histology Electron Microscopy In–Situ Hybridization and the Polymerase Chain Reaction," *Obstetrics and Gynecology 81*:402–408.
Rommelaere et al., 1991, "Antineoplastic Activity of Parvoviruses," *J. Virol. Methods 33*:233–251.
Rose, 1974, "Parvovirus Reproduction," *Publisher Unknown* :1–61.
Ruffing et al., 1992, "Assembly of Viruslike Particles by Recombinant Structural Proteins of Adeno–Associated Virus Type 2 in Insect Cells," *J. Virol. 66*:6922–6930.
Siegl et al., 1985, "Characteristics and Taxonomy of *Parvoviridae*," *Intervirology 23*:61–73.
Srivastava et al., 1983, "Nucelotide sequence and organization of the adeno–asociated virus 2 genome," *J. Virol. 45*:555–564.
Tobiasch et al., 1992, "Structural Features and Sites of Expression of a New Murine 65 kD and 48 kD Hair–related Keratin pair, Associated with a Special Type of Parakeratotic Epithelial Differentiation", *Differentiation 50*:163–178.
van den Brule et al., 1989, "Use of Anticontamination of Primers in the Polymerase Chain Reaction for the Detection of Human Papilloma Virus Genotypes in Cervical Scrapes and Biopsies," *J. Med. Virol. 29*:20–27.
Wright et al., 1990, "PCR Protocols, A Guide to Methods and Applications," *Academic Press Chapter 19, Part 1*:153–158.

* cited by examiner

Primary Examiner—Mary E. Mosher
(74) Attorney, Agent, or Firm—Albert P. Halluin; Birgit Millauer; Wilson Sonsini Goodrich & Rosati

(57) ABSTRACT

The present invention relates to a method of detecting a causative agent of the so-called spontaneous early abortion by investigating patients' samples for the presence of adeno-associated virias DNA (AAV DNA), or AAV antigen or antibodies, preferably of the IgM type, directed to AAV. Furthermore, the present invention relates to antibodies suitable for said method.

7 Claims, 1 Drawing Sheet

ADENO-ASSOCIATED VIRUS-ITS DIAGNOSTIC USE WITH EARLY ABORTION

Figure 1:
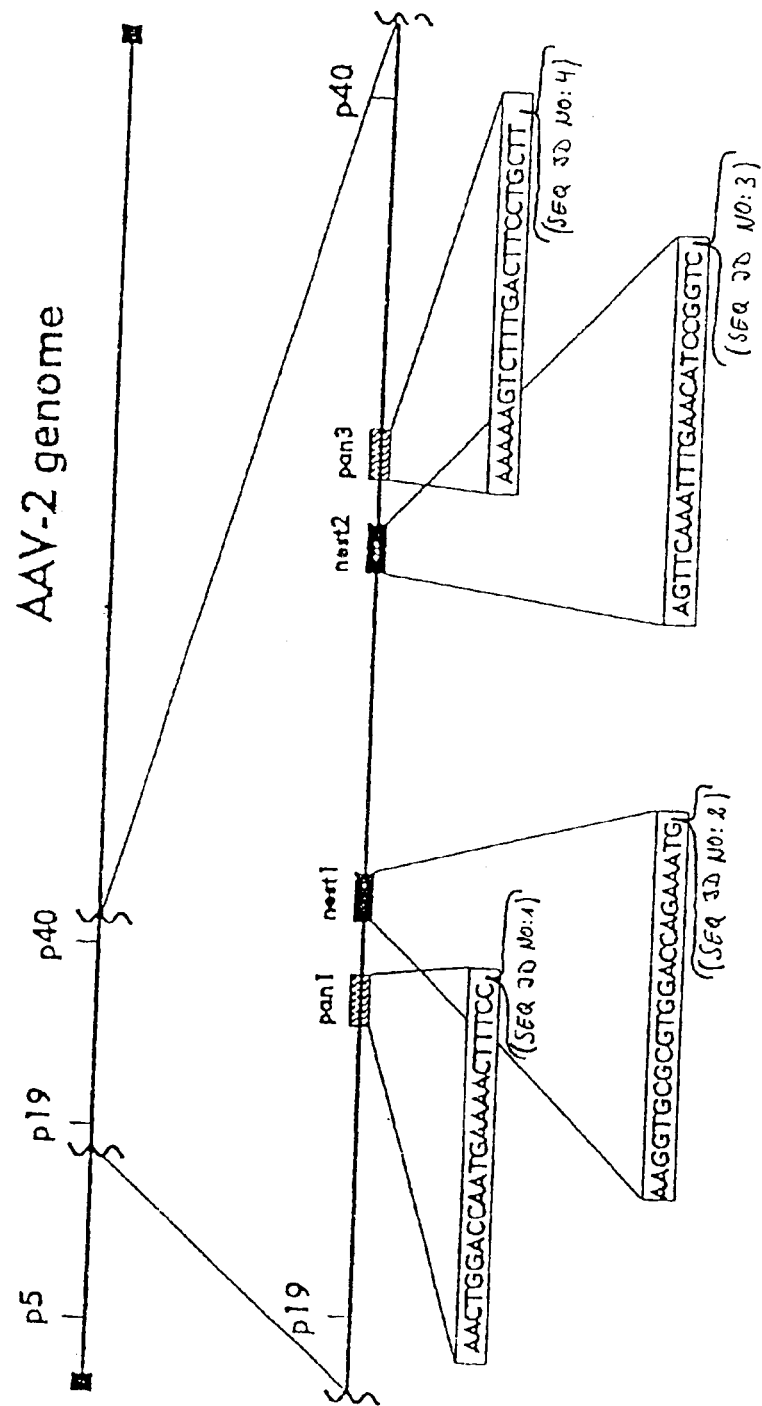

This is a national phase filing of the Application No. PCT/EP94/03564, which was filed with the Patent Corporation Treaty on Oct. 28, 1994, and is entitled to priority of European Patent Application 93117452.8, filed Oct. 28, 1993.

I. FIELD OF THE INVENTION

The present invention relates to a method of detecting a causative agent of the so-called spontaneous early abortion by investigating patients' samples for the presence of adeno-associated virus DNA (AAV DNA), or AAV antigen or antibodies, preferably of the IgM type, directed to AAV. Furthermore, the present invention relates to antibodies suitable for said method.

II. BACKGROUND OF THE INVENTION

The adeno-associated viruses (AAV) which are human parvoviruses that depend on coinfecting helper viruses for their replication, are thought to be non-pathogenic (Siegi et al., 1985, *Intervirology*, 23:61–73, Berns et al. 1987, *Adv. Virus Res.* 32:243–306) but rather to exhibit tumorsuppressive properties (Rommelaere et al., 1991, *J. Virol. Methods* 33:233–251). The virus may persist in infected individuals, possibly by integration of its DNA into specific chromosomal sites of the host cell genome as seen in cell culture. Recent studies of our laboratories have demonstrated that AAV is able to induce differentiation in a variety of cells of human and mouse origin (Klein-Bauemschmitt et al., 1992, *J. Virol.* 66:4191–4200) including embryonic stem cells. In the course of looking for putative targets of AAV infection, we analyzed material from spontaneous abortion for the presence of AAV DNA using for example the polymerase chain reaction (PCR), the Southern blotting technique and the in situ hybridization technique. Additionally, we analyzed serum samples from women with miscarriage and from other diseased or healthy women for the presence of antibodies to AAV using serological standard techniques such enzyme linked immunosorbent assay (ELISA), fluorescenceimmuno assay (FIA), radioimmune assay (RIA) or immunofluorescence assay (IFA).

Surprisingly, we found a significant correlation of both detectable AAV DNA in samples of abortion material and detectable IgM antibodies directed to AAV with the early abortion occurring during the first trimester of pregnancy. Accordingly, the present invention relates to a method of detecting the causative agent of spontaneous abortion.

III. SUMMARY OF THE INVENTION

The present invention relates to a method of detecting a causative agent of the so-called spontaneous early abortion by investigating patients' samples for the presence of adenoassociated virias DNA (AAV DNA), or AAV antigen or antibodies, preferably of the IgM type, directed to AAV. Furthermore, the present invention relates to antibodies suitable for said method.

IV. BRIEF DESCRIPTION OF THE DRAWINGS

FIG. 1 depicts PCR analysis of DNA (SEQ ID NOS: 1–4), prepared from histiligical sections of a spontaneous abortion (see, Example 1).

V. BRIEF DESCRIPTION OF THE INVENTION

The present invention relates to a method of detecting the causative agent of spontaneous abortion comprising the steps of (a) hybridizing a probe for an AAV polynucleotide to nucleic acids of a sample of abortion material under conditions which allow the formation of a heteroduplex between an AAV nucleic acid and the probe, and (b) detecting a polynucleotide duplex which contains the probe.

In a preferred embodiment of the present invention the method as mentioned above is a polymerase chain reaction (PCR), Southern blotting or in situ hybridization technique.

In another preferred embodiment of the present invention a hybridization technique is applied as described above, wherein one or more nucleic acid probes are used which are selected from the group consisting of the primers pan1 (SEQ ID NOS:1), pan2, nest1 (SEQ ID NO: 2) and nest2 (SEQ ID NO: 3). In FIG. 1 a schematic drawing of these primers, relative to the genome of the AAV type 2 (AAV-2) and the nucleotide sequences of the primers (SEQ ID NOS: 1–4) is presented.

The present invention further relates to a method of detecting the causative agent of spontaneous abortion comprising the steps of (a) incubating a probe antibody directed to an AAV antigen with a sample of abortion material under conditions which allow the formation of an antigen-antibody complex, and (b) detecting the antigen-antibody complex containing the probe antibody.

In step (a) one or more probe antibodies can be used. These antibodies can be directed to e.g. an AAV capsid or a single protein thereof, particularly VP1, VP2 or VP3. Examples of these antibodies are the following monoclonals, on deposit with the German Collection of Microorganisms and Cell Cultures ("DSMZ"):

A1; deposited at DSMZ—Deutsche Sammlung von Mikroorganismen und Zellkulturen GmbH under DSMZ ACC2195 on Oct. 13, 1994;

A69; deposited at DSMZ—Deutsche Sammlung von Mikroorganismen und Zellkulturen GmbH under DSMZ ACC2196 on Oct. 13, 1994;

B1; deposited at DSMZ—Deutsche Sammlung von Mikroorganismen und Zellkulturen GmbH under DSMZ ACC2197 on Oct. 13, 1994; and A20; deposited at DSMZ—Deutsche Sammlung von Mikroorganismen und Zellkulturen GmbH under DSMZ ACC2194 on Oct. 13, 1994

(see, TABLE 1). The address of the German Collection of Microogranisms and Cell Cultures is DSMZ—Deutsche Sammlung von Mikroorganismen und Zellkulturen, Mascheroder Weg lb. D-38124 Braunschweig, Germany.

The antibodies as mentioned above are subject matter of the present invention.

In a preferred embodiment of the present invention the method of antigen detection as mentioned above is an enzyme linked immunosorbent assay (ELISA), a radioimmuno assay (RIA), a fluorescence immuno assay (FIA) or an immunofluorescence assay (IEFA).

An example of the ELISA comprises the following steps.

(a) providing a substrate carrying the monoclonal antibody A 20, (b) contacting the substrate of (a) with a sample of abortion material to get an antigen-antibody complex, (c) contacting the complex of (b) with a polyclonal anti-AAV capsid antibody to get an antibody-antigen-antibody complex, (d) contacting the complex of (c) with an enzyme-labelled antibody directed to the polyclonal antibody of (c) to get a labelled complex of (c), and (e) contacting the complex of (d) with an enzyme-label-indicator to indicate the presence of said complex.

It is clear that the term "sample of abortion material" is only an example of materials which contain AAV capsids or parts thereof. Other examples are cells expressing recombinant AAV capsids or parts thereof.

The present invention, i.e. the antibodies alone or in combination with the AAV antigen detection method, is suitable to detect AAV capsids and/or parts thereof in any material.

Furthermore, the present invention relates to a method of detecting the causative agent of spontaneous abortion comprising the steps of (a) incubating a sample containing AAV or an antigenic part thereof with a sample suspected of containing anti-AAV antibodies under conditions which allow the formation of an antibodyantigen complex, preferably only containing antibodies of the IgM type, and (b) detecting an antibody-antigen complex, preferably Igm antibodyantigen complex, containing the probe antigen.

In step (a) the term "sample containing AAV or an antigenic part thereof" refers to AAV capsid proteins, particularly VP1, VP2 and/or VP3, preferably.

In another preferred embodiment of the present invention the method of detection of AAV specific antibodies, particularly IgM antibodies, is an ELISA, a RIA, a FIA or an IFA.

An example of the ELISA comprises the following steps:

(a) providing a substrate carrying an anti-human IgM antibody, (b) contacting the substrate of (a) with a patient's body-fluid to got an antibody-antibody complex, (c) contacting the complex of (b) with recombinant VP1, VP2 and/or VP3 to get a VP-antibody-antibody complex, (d) contacting the complex of (c) with an anti-VP-antibody to get an anti-VP-antibody-VP-antibody-antibody complex, (e) contacting the complex of (d) with an enzyme-labelled antibody directed to the anti-VP-antibody of (d) to get a labelled complex of (d), and (f) contacting the complex of (e) with an enzyme-label-indicator to indicate the presence of said complex.

It is evident that persisting anti-AAV IgM/IgG titers in serum are associated with predisposition to early abortions. Thus, the present invention can also be used for effective risk factor screening, development of methods for prevention of pregnancy failure, and information of patients about the risks of pregnancy failure.

Furthermore, the present invention relates to a kit for detecting the causative agent of spontaneous abortion by hybridization as described above, comprising a probe for an AAV polynucleotide in a suitable container.

The present invention further relates to a kit for detecting the causative agent of spontaneous abortion by immunological antigen detection as described above, comprising a probe antibody directed against an AAV antigen in a suitable container.

The present invention further relates to a kit for detecting the causative agent of spontaneous abortion by immunological antibody detection as described above, comprising AAV or an antigenic part thereof in a suitable container.

Modes for carrying out the invention. The art is rich in methods available to the man of the art in recombinant nucleic acid technology, microbiology and immunobiology for carrying out the present invention. Detailed descriptions of all of these techniques will be found in the relevant literature. See for example Maniatis, Fritsch & Sambrook: *Molecular Cloning: A Laboratory Manual* (1989); *DNA Cloning*, Vol. I and II (D. N. Glover ed., 1985); *Oligonucleotide Synthesis* (M. J. Gait ed., 1984); *Nucleic Acid Hybridization* (B. D. Hamos & S. J. Higgins eds., 1984); *Animal Cell Culture* (R. I. Freshney ed., 1986); J. D. Watson, J. Gilman, J. Witkowski, M. Zoller: *Recombinant DNA*, Second Edition (1992); *Immunochemical Methods in Cell and Molecular Biology* (Academic Press, London, 1387); *Protein Purification: Principles and Practice*, Second Edition (Springer Verlag, N.Y.); *Handbook of Experimental Immunology*, Vol. I–IV (D. M. Weir and C. C. Blackwell eds., 1986); *Immunoassay: A Practical Guide* (D. W. Chan and M. T. Perlstein eds., 1987). *ELISA and Other Solid Phase Immunoassays: Theoretical and Practical Aspects* (D. M. Kemeny and S. J. Challacombe eds., 1988); *Principles and Practice of Immunoassay* (C. P. Price and D. J. Newman eds., .1991).

More detailed information on specific methodological aspects of AAV, such as cell culture, virus growth, virus purification, isolation of proteins, can be found in the relevant literature, e.g. *Handbook of Parvoviruses*, Vol. I and II CRC Press, Boca Raton, Fla., Ed. P. Tijssen; Ruffing, et al., 1992, *J. Virol.* 66:6922–6930.

All reagents such as antigens, antibodies, probe antigens, probe antibodies, nucleic acid probes, primers and auxilliary reagents necessary to perform an immunoassay or a hybridization assay, possibly using amplification techniques for improved sensitivity may be filled into suitable containers or coated to any solid phase such as plastic, glass and cells, and packaged into kits together with instructions for conducting the test.

VI. EXAMPLES

A. Example 1: Detection by Polymerase-Chain-Reaction (PCR)—Analysis of AAV DNA in Biological, e.g., Curettage Material of Spontaneous Abortion The primers used in PCR (pan1 (SEQ ID NO: 1), pan3 (SEQ ID NO:4)) and nested PCR (nest1(SEQ ID NO:2), nest2 (SEQ ID NO:3)), respectively, were designed to hybridize to sequences of AAV-2 (SEQ ID NOS:5 and 7) and AAV-5 (SEQ ID NOS:6 and 8) DNA by allowing mismatches not leading to amplification of other (e.g. cellular) DNA sequences. The amplified products are distinguishable by Southern blot experiments. The primers were prepared according to standard procedures.

The primers were designed displaying mismatches (underlined) as shown below:

AACTGGACCAATGAAAACTTTCC (SEQ ID NO:1) pan1

1386 TGCGTAAACTGGACCAATGA GAACTTTCCCTTCAAC (SEQ ID NO:5) AAV-2

130 TGCGTAAACTGGACCAATGA AAACTTTCCCTTCAAC (SEQ ID NO:6) AAV-5

AAAAAGTCTTTGACTTCCTGCTT (SEQ ID NO:4) pan3

1729 AAAAAGTCTTTGACTCCTGCTT (SEQ ID NO:7) AAV-2

472 AAAAAGTCCTTGACTTCCTGCTT (SEQ ID NO:8) AAV-5

DNA prepared from histological sections (5 µm, of fresh or fixed, paraffin—embedded, deparaffinated material (Methods as described by D. H. Wright and M. M. Manos in "PCR Protocols, A Guide to Methods and Applications", edited by M. A. Innis, D. H. Gelfand, J. J. Snoisky and T. L.

White, Chapter 19, pp. 153–158; Academic Press, New York, 1990) were analysed by PCR using the primers pan1 (SEQ ID NO: 1) and pan3 (SEQ ID NO:4) combined, followed in AAV posititive cases by a repetition of the PCR (to confirm specificity) using the (internal) primers nest1 (SEQ ID NO: 2) and nest2 (SEQ ID NO: 3) (see, FIG. 1), respectively. PCRs were performed for 40 cycles (one cycle=92° C., 1 min; 62° C., 4 min; 92° C., 15 sec) (van den Brule et al., 1989 *J. Med. Virol.* 29:20–27). Amplified products were characterized by electrophoretic separation (2% agarose gel) and blotting onto a nylon membrane (Gene Screen, NEN, Dupont, Dreieich, Germany) followed by hybridization at high stringency with $^{32}$P-labelled probes (labelled using the Megaprime™ DNA Labelling System, Amersham, UK) of AAV-2 (pTAV2; Heilbronn et al., 1990, *J. Virol.* 64:3012–3018) or of AAV-5. This probe was cloned from DNA from purified AAV-5 virions, propagated with adenovirus type 12 and purified as described in de La Maze and Carter, 1980, *J. Virol.* 33:1129–1137 and in Rose (1974) *Parvovirus Reproduction*, pp. 1–61; In: H. Fraenkel-Conrat and R. R. Wagner, eds., Comprehensive Virology, Plenum Press, New York.

B. Example 2: Detection by Southern Blotting Analysis of AAV DNA in fresh Curettage Material Genomic DNA was isolated using standard procedures with minor modification (Laird et al., 1991, *Nucl. Acids Res.* 19:4293–4294) and digested with restriction enzymes allowing analysis of characteristic restriction sites within the AAV genome. After separation through 0.8% agarose gels, DNA fragments were blotted onto Nylon membranes (Gene Screen) and hybridized AAV-2 DNA (pTAV2, see, Example 1) or specific AAV-5 DNA (see, TABLE 2) labelled by random priming with [α-$^{32}$P] dCTP (Amershem, Braunschweig, Germany).

C. Example 3: Detection of AAV DNA by in Situ Hybridization in Sections of Biopsy Material, e.g. Curettage from Spontaneous Abortion In situ hybridization was performed as described (Tobiasch et al., 1992, *Differentiation* 50:163–178), however, with the modification that AAV-2 DNA was detected by RNA-DNA hybridization. After DNase treatment, the probes were subjected to limited alkaline hydrolysis. Upon linearisation of the plasmid pTAV2 (Heilbronn et al. 1990, supra, with EcoRV, riboprobes were obtained and labelled with [$^{35}$S]-UTP by in vitro transcription with T7 RNA polymerase (method as described in Boehringer Mannheim Procedure supplied with the "SP6/17 Transcription Kit"). Prior to hybridization, both probe and target DNA were denatured (93° C., 10 min). For in situ hybridization with [$^{32}$P-]-UTP labelled probes, the protocol was as described in Dürst et al. 1992, *Virology*, 189:132–140.

D. Example 4: Provision of Antibodies Directed to AAV Capsid Proteins

In order to generate monoclonal antibodies directed to AAV capside proteiss two BALB/C mice were injected subcutaneously (s.c.) with 150 µl of a mixture of gel purified recombinant capsid proteins in PBS containing 100 µg each of VP1, VP2 and VP3, mixed with an equal volume of complete Freund's adjuvant. After four weeks the mice were boosted s.c. with 25 µg of purified UV-inactivated AAV-2 in 50 µl PBS and 50 µl incomplete Freund's adjuvant. After four weeks the mice were injected intraperitoneally (i.p.) each with 10 µg of UV-Inactivated AAV-2 in 100 µl PBS. Three days later one mouse was killed and the spleen cells were fused with X63/Ag8 cells according to standard procedures (Harlow, E. and Lane, D. (1988), Cold Spring Harbor Laboratory, *Antibodies, A laboratory mannual*). Resultant hybridoma culture supernatants were screened by Western blotting, immunofluorescence and ELISA. The second mouse was immunized six months later with 100 µg of purified VP3 in PBS (i.p.) and monoclonal antibodies were prepared as described above.

E. Example 5: ELISA for the Detection of IgG Antibodies Directed to AAV 96-well microtiterplates (Nunc, Denmark) were coated with 50 µl CsCl—gradient purified AAV 2 (dilution 1:1000 in 0.05 M carbonate-buffer pH 9.6) or with 50 µl recombinant AAV 2 capsid proteins VP1-3 (1:8,000 in 0.05 M carbonate-buffer) and incubated overnight at RT. Plates were washed twice (washing buffer: PBS, 0.05% Tween 20) and human sera were added (50 µl/well, dilutions 1:25 to 1:800, dilution buffer: PBS, 2% BSA, 0.05% Tween 20) and incubated for 1 h at 37° C. in a wet chamber. After washing plates were incubated with 50 µl/well peroxydase conjugated monkey antihuman IgG antibody (1:2000) for 45 minutes at 37° C. in a wet chamber. Plates were washed four times and 50 µl substrate solution (5 mg OPD in 25 ml 0.1 M citratebuffer pH 5,0+10 µl $H_2O_2$ 35%) was added. Plates were stored for 10–15 minutes in the dark and the reaction was stopped with 50 µl 1N $H_2SO_4$/well. Extinctions were measured at 492 nm in a Titertek photometer. Background signal was determined by measuring the extinction without adding human sera and was substracted on every well (background signal extinction ranged from 0.035 to 0.05).

F. Example 6: ELISA for the Detection Of IgM Antibodies Directed to AAV

Version A

Plates were coated as described in Example 4. Human sera were added after they had been treated according to the following absorption protocol in order to eliminate remaining IgG-antibodies: 20 µl absorption reagent (FREKA-Fluor, Fresenius, Germany) were diluted with 25 µl PBS and 5 µl of human serum was added. Absorption was performed for at least 15 minutes at RT, and subsequently sera were tested at dilutions from 1:100 to 1:800. Incubation was performed for 1 h at 37° C. in a wet chamber and after washing 50 µl/well peroxydase conjugated goat anti human IgM antibody (1:2000 in PBS/2% BSA/0.05% TWEEN 20) were added. Plates were incubated for 45 minutes at 37° C. and washed four times. The OPD reaction and photometric evaluation were performed as described in Example 5.

Version B

µ-capture ELISA

Plate Coating

Rabbit anti-human IgM antibody (DAKO) was first denatured at a protein concentration of 600 µg/ml, incubating for 30 min at RT in 50 mM glycin/HCl pH 2.5 containing 100 mM NaCl then neutralized with 1 M Tris base. The denatured antibody was then desalted by passing the solution over a Sephadex PD 10 column equilibrated in the coating solution (10 mM Tris/HCl pH 8.5 containing 100 mM NaCl). The sample was eluted from the column in the same buffer. The solution was adjusted to a protein concentration of 6 µg/ml by dilution in coating buffer and 200 µl added to each well on a polystyrene microtiter plate (NUNC immuno flat-bottomed well). The plate was incubated at 37° C. for 24 h in a humid atmosphere, contents decanted and wells washed 4 times with 250 µl/well of Tris-buffered saline (TBS) (0.02 M Tris/HCl pH 7,4, 0.15 M NaCl) containing 0.05% Tween 20 (wash buffer). The wells were then blocked with TBS containing 1% Tween 20 and 5% Sucrose (blocking solution) by incubating at 4° C. followed by 2 washings in wash buffer (TBS containing 0.05% Tween 20).

Assay

The second step in the ELISA involved contacting patients' sera with the antibody-coated plate. During incubation, IgM was immunologically bound to the solid-phase antibody. After removal of the unbound material and washing of the microtiter plates, the plates were incubated with purified recombinant AAV nucleocapsid proteins VP1, VP2 and VP3. After removal of the unbound material and washing of the microtiter plates, complexes of human IgM antibody-VP complexes were detected by incubation with the A1, A69 and B1 antibodies. Unbound monoclonal antibodies were removed by aspiration and the plates were washed. The bound monoclonal antibodies were detected by incubating the plates with goat anti-mouse immunoglobulin antibodies conjugated to horseradish peroxidase (HRP). Following removal of unbound conjugate by washing, a solution containing $H_2O_2$ 3-3', 5-5' tetramethylbenzidine (TMB) was added. Reactions were stopped after a suitable interval by addition of sulfuric acid. The Cutoff value of the ELISA was calculated as the average optical density of five negative samples plus 3 standard deviations (to correct for any aspecific binding). Samples giving absorbance values higher then the cutoff were considered positive.

Specifically, the anti-human IgM on the plate was reacted with serum by adding 100 µl of serum samples diluted 1:200 in TBS containing 10 mg/ml bovine serum albumin, and incubating the serum-containing wells for 1 h at room temperature. After incubation, the serum samples were removed by aspiration and the wells were washed 5 times with washing solution (TBS+0.05% Tween 20). Aliquots of 100 µl of the VP1, VP2 and VP3 antigen mixture (conc of 10-10 nM VP1, VP2 and VP3) were added to each well and the plates were incubated at room temperature at least 2 h, followed by removal of excess probe by aspiration and 5 washes with TBS+0.05% Tween 20. Bound VP1, VP2 and VP3 was detected by addition of 100 µl of a mixture of hybridoma supernatants from A1, A69 and B1 monoclonal antibodies producing hybridomas (antibody conc 1-10 nM), followed by 5 standard washes of the plates with TBS+ 0.05% Tween 20. Monoclonal antibody binding was detected by addition of 200 µl of 1 1/2000 dilution of sheep anti-mouse IgG horseradish peroxidasc-conjugated antibody (Dako, Hamburg/Germany) and incubated for 1.5 h at room temperature, followed by 5 standard washes of the plate. Enzyme activity was revealed by addition of 100 µl of a solution of TMB (Serex, Maywood, N.J./USA). The plate was incubated until the desired color development was reached and terminated by addition of 50 µl 2N sulfuric acid. Optical densities ($OD_{450}$) of negative and positive control sera as well as samples were determined. The cutoff value as calculated from five negative sera was $OD_{450}$=0.40.

G. Example 7: ELISA for the Detection of AAV Capsids Plate Coating

100 µl of the A20 antibody (see, supra) equilibrated in coating buffer solution (50 mM $NaHCO_3$ pH 9.6 and adjusted to a protein concentration of 1.5 ng/ml was addad to each well on a polystyrene microtiter plate (NUNC immune flat-bottomed well). The plate was incubated at 4° C. for 24 h, contents decanted and wells, washed 5 times with 250 µl/well of phosphate-buffered saline (PBS) (wash buffer). The wells were blocked with 260 µl of 3% BSA in PBS (blocking solution) by incubating at least 30 minutes at room temperature followed by 6 washings in wash buffer.

Assay

A standard curve within the range of 10–10,000 capsids/ml was prepared by diluting AAV capsids in standard dilution solution containing PBS.

Unknown samples were diluted as appropriate in dilutent solution and 100 µl added to the test wells. When tissue culture supernatants were to be assayed, 100 µl of a 1:10 to $1:10^8$ dilution was to be added to the test well. The plate was incubated for 3 h at room temperature. The plate was washed 5 times in wash buffer and 100 µl rabbit anti-AAV-polyclonal antiserum at a dilution of 1/1000 in 3% BSA in PBS added to each well. The plate was incubated at room temperature for 2 h as previously and then washed 5 times in PBS Tween. AAV capsid was detected by addition of 100 µl of a 1/2000 dilution of a goat anti-rabbit IgG myeloperoxidase-conjugated antibody prepared in antibody diluent and incubated for 1 h at room temperature followed by 5 standards washes of the plate. Enzyme activity was revealed by addition of 100 µl of a 0.1 mg/ml solution of tetramethylbenzidine (TMB) prepared in 0.1 M Na-acetate buffer pH 6 to each well. The plate was incubated at room temperature until the desired color development was reached, longer incubation periods being necessary to detect lower concentration ranges, i.e. standards less than 10 capsids/ml. The concentration of unknown samples was determined by comparison of their optical density to the standard curve.

H. Example 8: Detection of AAV-DNA in Curettage Material of Spontaneous Absorption A total of 50 samples of curettage material of spontaneous absorption were analysed for the presence of AAV DNA either by PCR or Southern Blotting or both. 41 samples were from abortions in the first and 9 samples from abortions in the second and third trimester of pregnancy.

Among the 41 samples taken during the first trimester of pregnancy, 14 consisted of fresh material that could be tested by Southern Blotting, by which method 9 samples were shown to be positive. All other samples tested were sections from paraffin-embedded tissues, that were analysed by PCR. Among these, 30 samples were from abortions in the first trimester of pregnancy, of which 12 samples were shown to be positive for AAV DNA. All of the 9 samples from the second or third trimester of pregnancy were negative by PCR.

Thus, in 21 of 41 samples, i.e. 50% of spontaneous abortions in the first trimester of pregnancy AAV specific DNA sequences could be detected, whereas 9 spontaneous abortions in the second or third trimester were negative (see TABLE 3).

I. Example 9

A total serum of 148 serum samples drawn from healthy probands, diseased patients with various syndromes being unrelated to abortion, and pregnant women with spontaneous abortion during the first trimester of pregnancy were tested for antibodies directed to AAV.

The results obtained are displayed in TABLE 4. Generally, the prevalence of specific IgG antibodies was quite high, between 62 and 100% in the different groups of probands/patients. However, specific IgM antibodies were shown to be significantly correlated with "pregnancy problems".

TABLE 1

| Term | Subtype | Epitope | Western Blotting | Immuno-Precipitation | Immuno-Fluorescence | Characteristics |
|---|---|---|---|---|---|---|
| A1 | IgG2a | between aa 1–104 | + specific recognition of VP1 | + | + | recognition of monomeric and oligomeric VP1 |
| A69 | IgG1 | between aa 105–136 | + specific recognition of VP1 and VP2 | + + | + + | recognition of monomeric and oligomeric VP1 and VP2 |
| B1 | IgG1 | between aa 136–669 | + + recognition of VP1, VP2 and VP3 | + + | + + | recognition of monomeric and oligomeric VP1, VP2 and VP3 |
| A20 | IgG3 | presumable conformation | – (negativ) | + + + | + + | preferable recognition of AAV capsid, no reaction with recombinant monomeric capsid protein | aa: amino acid6

TABLE 2

308 bp part of BamH1b fragment of AAV5

```
    TCAATCAGGTGCCGGTGACTCACGAGTTTAAAGTTCCCAGGGAATTGGCGGGAACTAAAG
487                                                              546
    AGTTAGTCCACGGCCACTGAGTGCTCAAATTTCAAGGGTCCCTTAACCGCCCTTGATTTC

GGGCGGAGAAATCTCTAAAACGCCCACTGGGTGACGTCACCAATACTAGCTATAAAAGTC
547                                                              606
    CCCGCCTCTTTAGAGATTTTGCGGGTGACCCACTGCAGTGGTTATGATCGATATTTTCAG

TGGAGAAGCGGGCCAGGCTCTCATTTGTTCCCGACACGCCTCGCAGTTCAGACGTGACTG
607                                                              666
    ACCTCTTCGCCCGGTCCGAGAGTAAACAAGGGCTCTGCGGAGCGTCAAGTCTGCACTGAC

TTGATCCCGCTCCTCTGCGACCGCTCAATTGGAATTCAAGGTATGATTGCAAATGTGACT
667                                                              726
    AACTAGGGCGAGGAGACGCTGGCGAGTTAACCTTAAGTTCCATACTAACGTTTACACTCA

ATCATGCTCAATTTGACAACATTTCTAACAAATGTGATGAATGTGAATATTTGAATCGGG
727                                                              786
    TAGTACGAGTTAAACTGTTGTAAAGATTGTTTACACTACTTACACTTATAAACTTAGCCC

GCAAAAATGGATGTATCTGTCACAATGTAACTCACTGTCAAATTTGTCATGGGATTCCCC
787                                                              846
    CGTTTTTACCTACATAGACAGTGTTACATTGAGTGACAGTTTAAACAGTACCCTAAGGGG

CCTGGGAAAAGGAAAACTTGTCAGATTT
847                                                              874
    GGACCCTTTTCCTTTTGAACAGTCTAAA
```

TABLE 3

Prevalence of AAV DNA in curettage materials

| | Detection of AAV DNA by (number AAV positive/number analysed) | | |
|---|---|---|---|
| Diagnosis/Pathology | PCR | Southern Blotting | Total |
| spontaneous abortion (1st trimester of pregnancy) | 12/30 | 9/14 | 21/41* |
| abortion 2nd trimester | 0/3 | n.d. | 0/3 |
| abortion 3rd trimester or placenta post partum | 0/6 | n.d | 0/6 | n.d. = not done;
*= 3 samples positive with PCR were tested by Southern blotting analysis

TABLE 4

| | | Serum Antibodies to AAV Diagnosis | | | | | | | |
|---|---|---|---|---|---|---|---|---|---|
| | n | IgG− IgM− | IgG+ IgM− | IgG− IgM+ | IgG+ IgM+ | IgG+ n | % | IgM+ n | % |
| Controls (all) | 58 | 8 | 45 | 2 | 3 | 48 | 83 | 5 | 8.6 |
| Employees | 32 | 4 | 24 | 2 | 2 | 26 | 81 | 4 | 12.5 |
| Patents *) | 26 | 4 | 21 | 0 | 1 | 22 | 85 | 1 | 4 |
| breast (all) | 38 | 1 | 32 | 0 | 5 | 37 | 97 | 5 | 13.2 |
| mammary dystrophy | 19 | 1 | 13 | 0 | 5 | 18 | 75 | 5 | 26 |
| breast cancer | 19 | 0 | 19 | 0 | 0 | 19 | 100 | 0 | 0 |
| cervix uteri (all) | 26 | 2 | 17 | 4 | 3 | 20 | 77 | 7 | 27 |
| normal (or metaplasia) | 3 | 1 | 2 | 0 | 0 | 2 | 67 | 0 | 0 |
| CIN/CIS | 22 | 1 | 14 | 4 | 3 | 17 | 77 | 7 | 32 |
| cancer | 1 | 0 | 1 | 0 | 0 | 1 | 100 | 0 | 0 |
| pregnancy problems (all) | 26 | 6 | 12 | 2 | 6 | 18 | 69 | 8 | 31 |
| Extra uterine | 2 | 0 | 2 | 0 | 0 | 2 | 100 | 0 | 0 |
| chromosomal aberrations | 3 | 0 | 2 | 0 | 1 | 3 | 100 | 1 | 33 |
| abortion (1st trimester) of unclear etiology | 21 | 6 | 8 | 2 | 5 | 13 | 62 | 8 | 38 |

*) with uterus myoma, or normal pregnancy, hysterectomy (normal)

What is claimed is:

1. An isolated monoclonal antibody directed against an AAV type 2 capsid or a protein thereof, capable of detecting said AAV type 2 capsid or a protein thereof in ELISA assay, immunofluorescence or Western blotting.

2. The antibody of claim 1, wherein said antibody is A1 as deposited with DSMZ under deposit number ACC2195.

3. The antibody of claim 1, wherein said antibody is A20 as deposited with DSMZ under deposit number ACC2194.

4. The antibody of claim 1, wherein said antibody is A69 as deposited with DSMZ under deposit number ACC2196.

5. The antibody of claim 1, wherein said antibody is B1 as deposited with DSMZ under deposit number ACC2197.

6. A kit for detecting an AAV antigen comprising a monoclonal antibody directed to an AAV type 2 capsid or a protein thereof, capable of detecting said AAV type 2 capsid or a protein thereof in ELISA assay, immunofluorescence or Western blotting, in a suitable container.

7. The kit of claim 6, wherein said monoclonal antibody is A1 as deposited with DSMZ under deposit number ACC2195, A20 as deposited with DSMZ under deposit number ACC2194, A69 as deposited with DSMZ under deposit number ACC2196 or B1 as deposited with DSMZ under deposit number ACC2197.

* * * * *

SEQUENCE LISTING

<160> NUMBER OF SEQ ID NOS: 9

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Primer pan1

<400> SEQUENCE: 1
aactggacca atgaaaactt tcc                                           23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer nest1

<400> SEQUENCE: 2
aaggtgcgcg tggaccagaa atg                                           23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Primer nest2

<400> SEQUENCE: 3
agttcaaatt tgaacatccg gtc                                           23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer pan3

<400> SEQUENCE: 4
aaaaagtctt tgacttcctg ctt                                           23

-continued

```
<210> SEQ ID NO 5
<211> LENGTH: 36
<212> TYPE: DNA
<213> ORGANISM: Adeno-Associated Virus-2

<400> SEQUENCE: 5
tgcgtaaact ggaccaatga gaactttccc ttcaac                                36

<210> SEQ ID NO 6
<211> LENGTH: 36
<212> TYPE: DNA
<213> ORGANISM: Adeno-Associated Virus-5

<400> SEQUENCE: 6
tgcgtaaact ggaccaatga aaactttccc ttcaac                                36

<210> SEQ ID NO 7
<211> LENGTH: 23
<212> TYPE: DNA
<213> ORGANISM: Adeno-Associated Virus-2

<400> SEQUENCE: 7
aaaaagtctt tgacttcctg ctt                                              23

<210> SEQ ID NO 8
<211> LENGTH: 23
<212> TYPE: DNA
<213> ORGANISM: Adeno-Associated Virus-5

<400> SEQUENCE: 8
aaaaagtcct tgacttcctg ctt                                              23

<210> SEQ ID NO 9
<211> LENGTH: 388
<212> TYPE: DNA
<213> ORGANISM: Adeno-Associated Virus-5

<400> SEQUENCE: 9
tcaatcaggt gccggtgact cacgagttta aagttcccag ggaattggcg ggaactaaag      60
gggcggagaa atctctaaaa cgcccactgg gtgacgtcac caatactagc tataaaagtc     120
tggagaagcg ggccaggctc tcatttgttc ccgagacgcc tcgcagttca gacgtgactg     180
ttgatcccgc tcctctgcga ccgctcaatt ggaattcaag gtatgattgc aaatgtgact     240
atcatgctca atttgacaac atttctaaca aatgtgatga atgtgaatat ttgaatcggg     300
gcaaaaatgg atgtatctgt cacaatgtaa ctcactgtca aatttgtcat gggattcccc     360
cctgggaaaa ggaaaacttg tcagattt                                       388
```